United States Patent [19]

Nelson, III

[11] Patent Number: 5,269,788
[45] Date of Patent: Dec. 14, 1993

[54] ADJUSTABLE HEMOSTATIC CIRCUMCISION DRESSING AND METHOD OF ITS USE

[76] Inventor: James H. Nelson, III, 5995 Strome Ct., Dublin, Ohio 43017

[21] Appl. No.: 929,707

[22] Filed: Aug. 12, 1992

Related U.S. Application Data

[63] Continuation-in-part of Ser. No. 775,768, Oct. 15, 1991, abandoned.

[51] Int. Cl.$^5$ .......................................... A61B 17/326
[52] U.S. Cl. ..................... 606/118; 606/157; 403/DIG. 9; 24/531
[58] Field of Search ....................... 606/118, 157, 221; 403/DIG. 9; 24/484, 531, 546, 28

[56] References Cited

U.S. PATENT DOCUMENTS

| | | | |
|---|---|---|---|
| 428,123 | 5/1890 | Morrison | 24/28 |
| 2,353,647 | 7/1944 | Carmichael | 606/118 |
| 2,561,176 | 7/1951 | Buckingham | 606/118 |

FOREIGN PATENT DOCUMENTS

| | | | |
|---|---|---|---|
| 1232234 | 5/1986 | U.S.S.R. | 606/118 |

Primary Examiner—Randall L. Green
Assistant Examiner—D. Willse
Attorney, Agent, or Firm—Mueller and Smith

[57] ABSTRACT

The present invention is directed to a circumcision dressing, adjustable in circumference, which is placed around the subglanular or subcoronal region of a penis on its mucosal aspect. The dressing comprises an inner arcuate member, or ring, which is adapted to be positioned between the prepuce and shaft of the penis parallel to the corona of the glans. This inner ring is discontinuous, preferably at its dorsal aspect, to allow for insertion of an elongate hollow connector piece to increase circumference for different sized penises, and is made from polymer, rubber, or metal. If desired, the inner ring may bear a guard flange which extends anteriorly beneath the prepuce to protect the penis from injury during the circumcision procedure. After this first ring is applied to the mucosal aspect of the prepuce with the foreskin retracted, the prepuce is reduced, or pulled forward. A second ring, or outer arcuate member, of polymer, rubber, or metal is then applied. This outer ring is of the same shape as the inner ring but is hollow and snaps over the inner ring and its overlying foreskin. Both the inner and outer ring may be either essentially totally planar or may each contain a bend outside of such plane to follow the contours of the frenulum of the prepuce, or foreskin. Placement of the outer ring traps the foreskin and applies a compressive force thereto. This outer ring can be trimmed to adjust for size and is preferably scored adjacent one of its ends to facilitate such size adjustment. After application of the outer ring, the foreskin is excised with a sharp instrument such as a scalpel or scissors or with a surgical cautery. The rings, securely in position, act as both a line of sutures and a sterile dressing for the circumcision. Between the rings, pressure necrosis and healing occur in the course of approximately two to three weeks. On a return visit to the physician, the outer and inner rings are removed to reveal the healed circumcision.

10 Claims, 3 Drawing Sheets

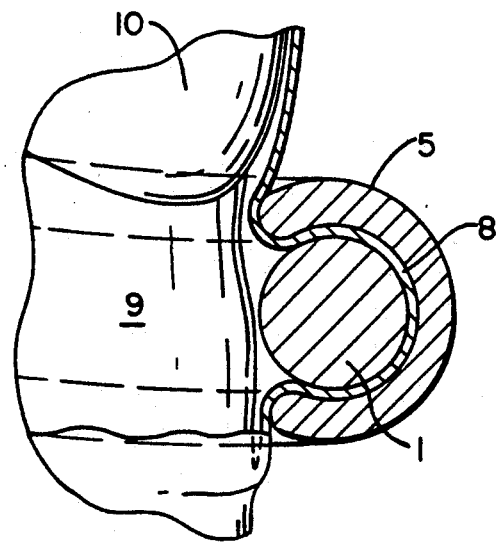
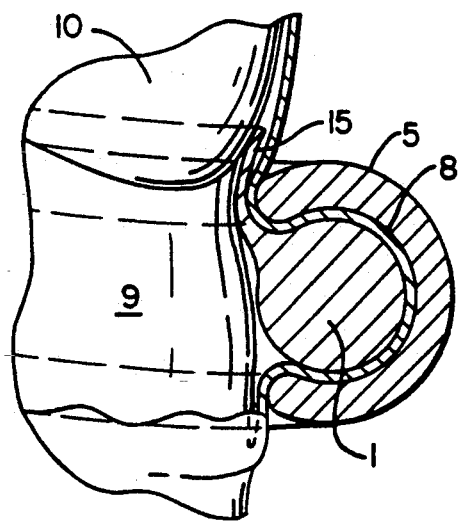
FIG. 6A   FIG. 6B
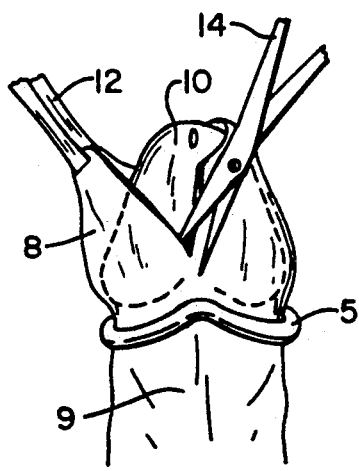
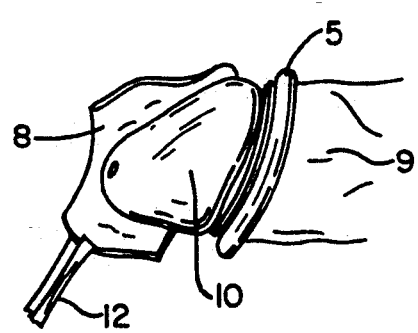
FIG. 7   FIG. 8
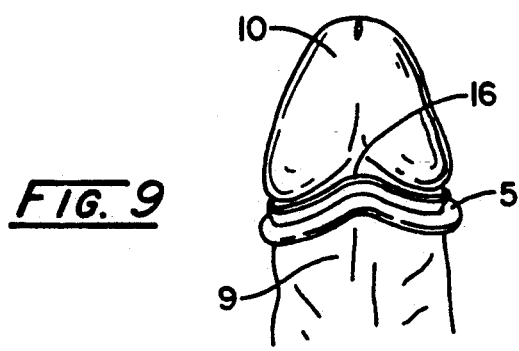
FIG. 9

ADJUSTABLE HEMOSTATIC CIRCUMCISION DRESSING AND METHOD OF ITS USE

CROSS-REFERENCE TO RELATED APPLICATIONS

This application is a continuation-in-part of copending application Ser. No. 07/775,768, filed on Oct. 15, 1991, now abandoned, the disclosure of which is expressly incorporated herein by reference.

BACKGROUND OF THE INVENTION

Circumcision has been practiced for religious and/or health purposes for centuries. In the United States, it is the most common operation performed on male infants and is performed on older children and adults with some regularity as well. The present invention relates to a surgical dressing which is particularly designed to facilitate and expedite the operation of circumcision in these older children including, e.g., frenulectomies and splitting unretractable dorsal foreskin as a part thereof.

An instrument in common use in the surgical art to facilitate circumcision is known generally as a circumcision clamp. This instrument is designed to position the parts of the penis to facilitate circumcision, the actual circumcision being effected by means of a scalpel or other cutting instrument which is extraneous to the clamp itself and separately manipulated by the surgeon.

In infants, circumcision is most commonly performed using a metal bell-shaped Gomco clamp, similar to that shown in U.S. Pat. No. 2,294,852, which crushes the thin infant foreskin and fuses the outer and inner layers, eliminating the need for suturing. Another device used in infants, disclosed in U.S. Pat. No. 3,056,407 and known as a "Plastibell," depends on a ligature to crush the foreskin.

The thickness and vascularity of the foreskin in the adult and older child, as well as the variability in size and shape of the glans penis, preclude the use of such fixed-sized crushing circumcision clamps. Thus, circumcision in adults and children ordinarily entails minor surgery, usually accomplished on an outpatient basis using local anesthesia in the adult or general anesthesia in the child. The usual operating time is between 15 and 20 minutes. Excision of the foreskin can be relatively bloody, and the placement of multiple absorbable sutures is tedious and routine. These sutures lose their tensile strength unpredictably, resulting often in secondary wound separation or bleeding from one to three weeks after surgery. Infection can be a hazard following circumcision due to difficulty in effectively dressing the penis, particularly in active children or adults. Further, the cost of outpatient circumcision, including surgeon's fee, operating room charges, and anesthesia can approach $1,500, depending on the geographical region.

Moreover, the reasons behind adult circumcision need to be examined carefully. Two of such reasons include non-retractable foreskin and tight frenulum which tends to tear. These reasons must be addressed in the adult circumcision device in general and in the specific treatments of these conditions. Large, bulky clamps do not comport with desires and practicalities of juveniles and adults requiring these procedures. The circumcision clamp in SU 1232-234 is an example of a clamp that, not only does adjust to different sized penises, but contains large bulky projections through which a screw fits. Such bulky projections would be rejected by male juveniles and adults requiring circumcision.

Thus, there exists a need for an adjustable hemostatic dressing device which would enable performance of circumcision on children and adults on an outpatient basis, with local anesthesia only, in a non-operating room (i.e., office) environment, without the need for sutures or additional dressings. Such a device would not only offer time savings and cost reduction, but lowered morbidity as well. It is estimated that such a device could provide cost reductions approaching 90% and time savings in the range of 60%-80%.

BROAD STATEMENT OF THE INVENTION

The present invention is directed to a circumcision dressing, adjustable in circumference, which is placed around the subglanular or subcoronal region of a penis on its mucosal aspect. The dressing comprises an inner arcuate member or ring, which is adapted to be positioned between the prepuce and shaft of the penis parallel to the corona of the glans. This inner ring is discontinuous, preferably at its dorsal aspect, to allow for insertion of an elongate hollow connector piece to increase circumference for different sized penises, and is made from polymer, rubber, or metal. If desired, the inner ring may bear a guard flange which extends anteriorly beneath the prepuce to protect the penis from injury during the circumcision procedure.

After this first ring is applied to the mucosal aspect of the prepuce with the foreskin retracted, the prepuce is reduced, or pulled forward. A second ring, or outer arcuate sleeve, also of polymer, rubber, or metal, then is applied. This outer sleeve is of the same shape as the inner ring but is hollow and snugly snaps over the inner ring and its overlying foreskin. Both the inner and outer ring may be either essentially totally planar in configuration or may each contain a bend outside of such plane to follow the contours of the frenulum of the prepuce or foreskin. Placement of the outer ring traps the foreskin and applies a compressive force thereto. This outer ring can be trimmed to adjust for size and is preferably scored adjacent one of its ends to facilitate such size adjustment. After application of the outer ring, the foreskin is excised with a sharp instrument such as a scalpel or scissors or with a surgical cautery.

The rings, securely in position, act as both a line of sutures and a sterile dressing for the circumcision. Between the rings, pressure necrosis and healing occur in the course of approximately two to three weeks. On a return visit to the physician, the outer and inner rings are removed to reveal the healed circumcision.

Another aspect of the present invention involves the application of the principals of the new circumcision dressing and broadens it to a dressing that is universally adapted for use in the severance of penile skin in other surgical procedures related to circumcisions, such as, frenulectomies and splitting unretractable dorsal foreskin. Such hemostatic dressing for penile skin (prepuce) severance, comprises an outer elongate longitudinally-slotted sleeve; and an inner elongate member adapted to press-fit tightly into said sleeve. Penile skin is available for placing in between said sleeve and said member whereby a crushing action is exerted upon said skin to cause hemostasis for said skin to be severed.

Primary objects of this invention include elimination of the necessity for suture and provision of inherent dressing means. A further object of this invention is the provision of a surgical device for circumferentially clamping the prepuce quickly and efficiently whereby a neat incision can easily be made and where the loss of blood can be minimized due to the hemostasis caused by the clamping pressure of the device. A still further object of the invention resides in the provision of a guard member for the penis shaft so as to prevent accidental injury thereto during the cutting operation.

Additional objects of the invention include the provision of a surgical dressing which insures against traumatic infection of the wound caused by the severing of the prepuce, and which can be more conveniently and more comfortably worn by the patient following the operation, thus eliminating the necessity of any post-operative care. Still further objects of the invention reside in the provision of a surgical device that is strong, durable, highly efficient in operation, extremely simple in construction and inexpensive to manufacture, easy to use, and having a minimal number of parts.

Also within the purview of the present invention is a method for clamping the prepuce of a penis during circumcision with an adjustable dressing, which method comprises the steps of:

(a) retracting the prepuce;

(b) placing an inner arcuate member between the prepuce and the shaft of the penis parallel to the corona of the glans of said penis, said inner member having a pair of ends;

(c) inserting the ends of said inner member into an elongate connector piece:

(d) extending the prepuce over said inner member;

(e) press-fitting said inner member into the groove of an outer arcuate member having a groove disposed about its inner periphery, said prepuce being crushed thereby to cause hemostasis;

(f) excising the foreskin; and (g) removing said outer and inner members after necrosis and healing of the skin have occurred.

The circumcision dressing of the present invention also can be provided in a form making it ideally suitable for use in frenulectomies and in splitting the dorsal foreskin when the foreskin is unretractable, two of the major causes for juvenile and adult circumcisions. Such hemostatic dressing for penile skin severance comprises:

(a) an outer elongate longitudinally-slotted sleeve; and (b) an inner elongate member adapted to press-fit tightly into said sleeve, penile skin available for placing in between said sleeve and said member whereby a crushing action is exerted upon said skin to cause hemostasis for said skin to be severed.

BRIEF DESCRIPTION OF THE DRAWINGS

FIGS. 6A and 6B show the circumcision dressing in cross-section with the parts thereof operatively emplaced ready for an operation to be performed, where FIG. 6A illustrates a simple round embodiment of the inner ring, whereas in FIG. 6B the inner ring has been modified to bear a guard flange which extends anteriorly beneath the prepuce to protect the penis from injury during the circumcision operation;

FIG. 7 is an elevational ventral view portraying the actual circumcision operation wherein, following the press-fitting of the inner ring into the groove of the outer ring to crush the prepuce sufficiently to cause hemostasis, the foreskin is excised;

FIG. 8 is a side lateral view of the circumcision operation showing removal of the excised foreskin;

FIG. 9 is an elevational ventral view of the penis showing the condition of the membranes subsequent to the circumcision operation. Note that the circumcision dressing of the present invention will remain in place until necrosis and healing of the severed skin have occurred;

DETAILED DESCRIPTION OF THE INVENTION

Figure 1:
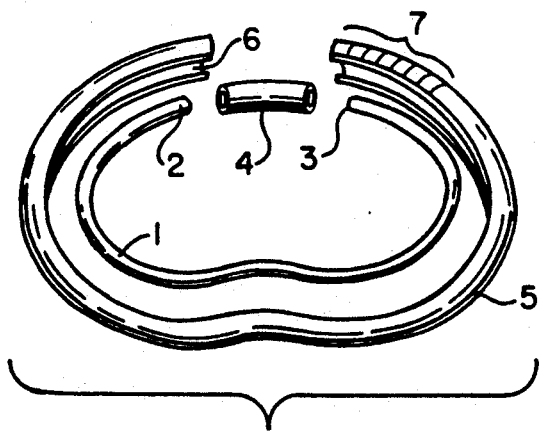
FIG. 1 is a perspective view showing the three components of the adjustable circumcision dressing of the present invention, viz., an inner ring, a connector piece which is inserted into the inner ring to vary its circumference for different sized penises, and an outer ring.

In the performance of a circumcision operation, it is desirable that the prepuce first be crushed in a line about the base of the glans and, after an interval of time necessary to effect hemostasis, that the prepuce be amputated adjacent, and on the distal side of, the region of hemostasis. It is desirable, also, if not essential, that the frenulum not be severed or injured during the acts of hemostasis and amputation of the prepuce. To this end, it is necessary that the prepuce be properly arranged prior to hemostasis.

Referring to the drawings wherein like numerals designate like parts, it can be seen in certain of the views that the penis includes shaft or body 9, glans or head 10, and prepuce or foreskin 8 which is to be removed during the circumcision. Prepuce 8 has an outer skin and a mucous membrane lining. At the inner end of glans 10 is the rim or rounded projecting border 11 which is known as the corona.

FIG. 1 shows inner arcuate member 1, having a pair of ends 2 and 3, which connect to elongate hollow connector piece 4 in order to accommodate penises of different sizes. Outer arcuate member 5 has disposed about its inner periphery groove 6. Adjacent one of its ends, outer member 5 retains scoring marks 7 to facilitate sizing for the aforementioned penises of different sizes.

Figure 2:
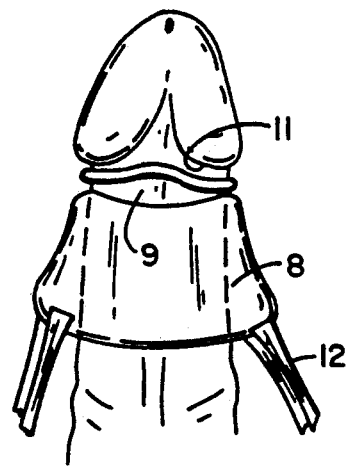
FIG. 2 is an elevational ventral view showing the prepuce or foreskin retracted with forceps and the inner ring of the adjustable circumcision dressing in place.
Figures 3A, 3B:
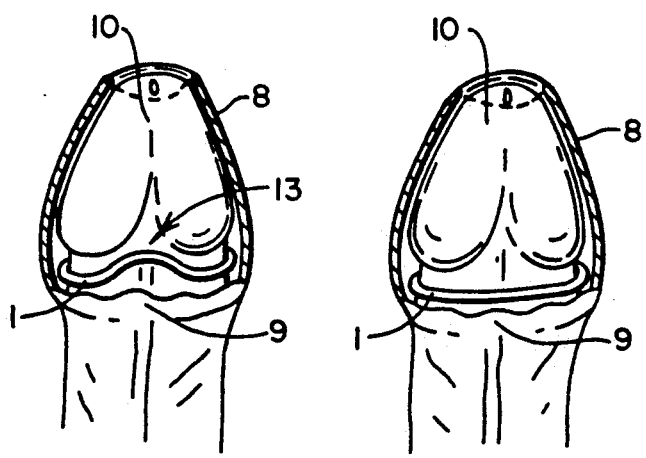
FIGS. 3A and 3B are elevational ventral views where the prepuce has been reduced, or pulled forward to its original position, following application of the inner ring, where in FIG. 3B the inner ring is essentially totally planar in configuration, whereas in FIG. 3A the inner ring departs from planar configuration to more closely follow the contours of the glans and to accommodate the frenulum.
Figures 4, 5:
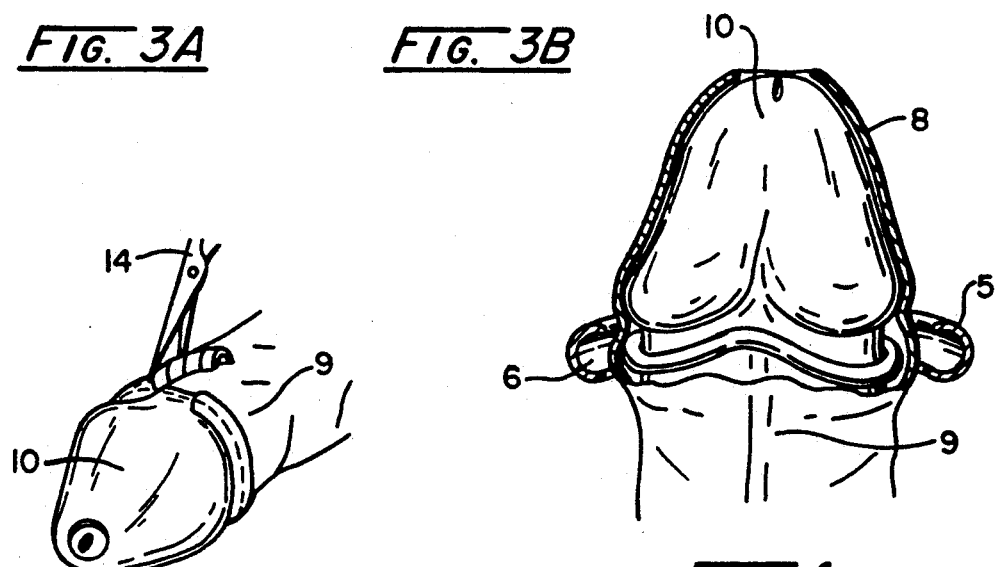
FIG. 4 is a fragmentary elevational ventral view of the outer ring as it is being positioned around the inner ring and prepuce, illustrating the manner in which the inner ring is press-fitted into the groove of the outer ring.
FIG. 5 is an anterior perspective view of the circumcision dressing of the present invention properly positioned on the glans preparatory to a final fitting of the outer ring.

Utilizing the method of the present invention, the operation can easily be performed in an aseptic manner. As illustrated in FIG. 2, prepuce 8 first is retracted with forceps 12 to expose glans 10. Inner arcuate member 1 next is placed over glans 10 and may contain contour 13 along the ventral surface to receive the frenulum, as shown in FIG. 3A. Prepuce 8 then is pulled forward over the glans, as shown in FIGS. 3A and 3B, and outer arcuate member 5 is applied around the prepuce, as shown in FIG. 4. Inner arcuate member 1 then is press-fitted into groove 6 of outer arcuate member 5, thereby crushing prepuce 8 to cause hemostasis. FIG. 5 simply shows the final fitting of outer arcuate member 5 whereby a cut is made using scissors 14 along scoring marks 7 to achieve a perfect fit.

After an interval of from about ten to twenty minutes, hemostasis occurs in the band of prepuce trapped by the device of the present invention. Using a scalpel or scissors 14, as shown in FIG. 7, the surgeon then may amputate the distal redundant prepuce. If necessary, any adhesions between the glans and the prepuce first are separated and a dorsal slit may be made in the prepuce subsequent to a first longitudinal crushing with a hemostat on the dorsal portion. If inner arcuate member 1 bears guard flange 15, as shown in FIG. 6B, amputation is performed by pressing the cutting edge of the scalpel or scissors 14 against flange 15 to prevent accidental injury to glans 10 and shaft 9. Thus a precise, accurate cut can be made at a, for example, 60° angle to shaft 9 of the penis immediately adjacent the portion of prepuce 8 where hemostasis has taken place.

It will be apparent that there will be no hemorrhage following the operation and that those portions of the membranes lying between the rings and the line of severance will become gangrenous and thereafter be sloughed off due to the clamping nature of inner arcuate member 1 and outer arcuate member 5, as shown at FIGS. 6A and 6B.

The inventive dressing or device ordinarily may be left in place from 2 to 3 weeks, depending on the age of the patient, or until the wound is well closed and capable of maintaining itself in proper relationship without extraneous support. No further dressing or post-operative care should be necessary when using the inventive dressing. Adventitious growths and adhesions are avoided completely by the mechanical separation of prepuce 8 from glans 10. The normal excretory functions of the organ are uninterrupted and devoid of the usual unsanitary aspects of textile dressings. Outer ring 5 is removed followed by inner ring 1 along with the devitalized tissue during a routine visit to the physician, resulting in a clean, well-healed line of excision.

It, thus, is seen that the circumcision dressing constituting this invention is easily applied and lends itself to a rapid and safe technique, and also eliminates the necessity of any post-operative care. It can be disposed of after use at negligible cost since it is of such simple and inexpensive construction. The circumcision dressing of the present invention, in practice, probably would be provided in two basic sizes, adult and pediatric, with individual inserts adjustable to encompass variation within these age groups.

Figure 10:
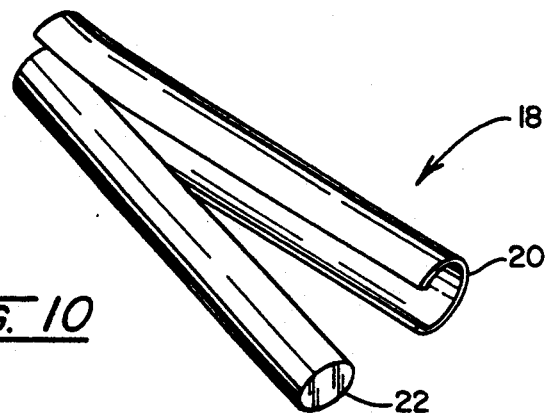
FIG. 10 is a perspective view of the functional elements of the hemostatic dressing for use in penile skin severance.
Figure 11:
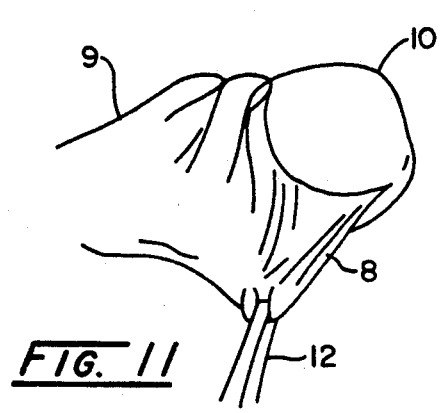
FIG. 11 is an anterior perspective view of the prepuce being stretched from the frenulum with forceps for later application of the hemostatic dressing for a frenulectomy.
Figure 12:
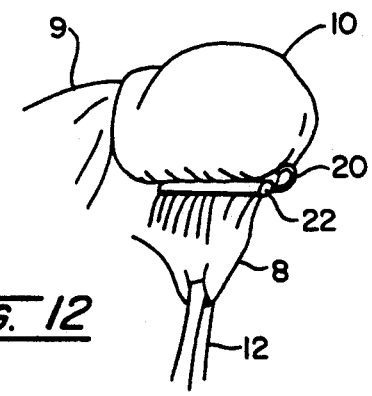
FIG. 12 shows application of the hemostatic dressing to the stretched prepuce of FIG. 11.
Figure 13:
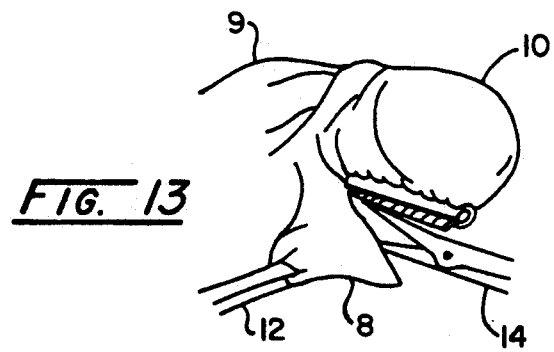
FIG. 13 shows the frenulectomy wherein the stretched prepuce of FIG. 12 is severed adjacent the hemostatic dressing with scissors.

Suitably adapted, the circumcision device of the present invention additionally can be used as a surgical dressing, for example, in frenulectomies and in splitting dorsal foreskin when the foreskin is unretractable, such as is illustration in FIGS. 10-15. Referring initially to FIG. 10, hemostatic dressing 18 is seen to be composed of outer elongate longitudinally slotted sleeve 20 and inner elongate member 22 which press fits into sleeve 20 in the same manner as do inner arcuate member 1 and outer arcuate member 5 illustrated at FIG. 1. These members also can be suitably scored for providing precise length dressings. When prepuce 8 is non-retractable, it can be stretched with forceps 12 as illustrated at FIG. 11. As illustrated at FIG. 12, slotted sleeve 20 is placed along stretched prepuce 8 at the base of glans 10 and then inner member 22 is press fitted into slotted sleeve 20 with the skin of prepuce 8 at the base of glans 10 trapped therebetween, thereby crushing prepuce 8 to cause hemostasis. Scissors 14 then can be used by the surgeon to amputate the distal redundant prepuce.

Figure 14:
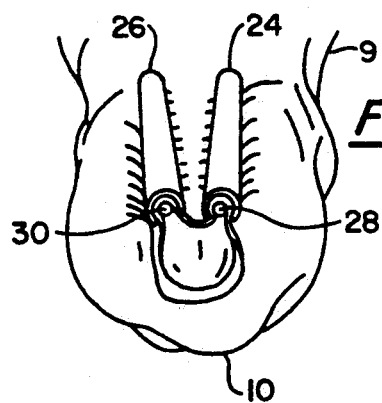
FIG. 14 is an anterior perspective view showing unretractable dorsal foreskin having a pair of the hemostatic dressings in position generally parallel with the glans.
Figure 15:
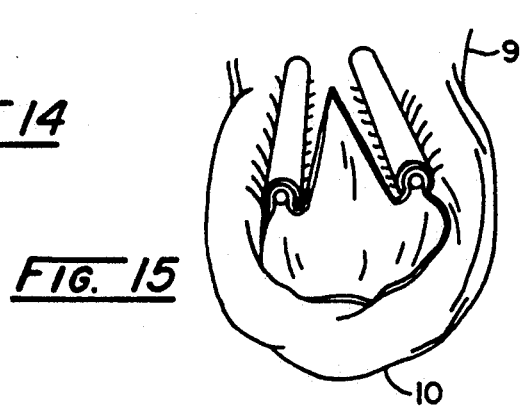
FIG. 15 shows splitting of the dorsal foreskin in between the pair of hemostatic dressings of the present invention.

When prepuce 8 is unretractable, a pair of hemostatic dressings (composed of slotted members 24 and 26, and inner members 28 and 30, respectively) can be similarly applied to the dorsal aspect foreskin 8 as illustrated at FIG. 14 and the dorsal foreskin split by the surgeon as illustrated at FIG. 15. Regardless of the use of hemostatic dressing 18, there again will be no hemorrhage following the procedure and that those portions of the membranes lying between the members and the line of severance will become gangrenous and thereafter be sloughed off due to the clamping nature of the dressing, as occurs when using the dressing illustrated at FIG. 1.

The novel dressing may be fabricated from any suitable material including metal and rubber, but preferably from most any suitable plastic which has the characteristic of being sufficiently soft so that it can be manually cut by scissors and also sufficiently brittle so that alternate bending will effect fracture. The material from which the article is manufactured should further have the characteristic of being lightweight and should possess an extremely smooth final finish or surface to avoid any irritation in its use. It has been found that the article can be cheaply and easily manufactured by the use of molds by many of the numerous methods well known in the plastics industry.

Since from the foregoing the construction and advantages of this surgical device are readily apparent, further description is believed to be unnecessary. However, since numerous modifications will readily occur to those skilled in the art after a consideration of the foregoing specification and accompanying drawings, it is not intended to limit the invention to the precise embodiment shown and described, but rather all suitable modifications and equivalents may be resorted to which fall within the scope of the appended claims.

I claim:

1. An adjustable circumcision dressing comprising:
    (a) an inner arcuate member having a pair of ends, said inner member adapted to be positioned between the prepuce and shaft of a penis parallel to the corona of the glans of said penis;

(b) an elongate hollow connector piece adapted to receive said pair of ends of said inner member to accommodate different sized penises; and (c) an outer arcuate grooved member adapted to be positioned over and encompass the prepuce when it is pulled up over said inner member, said groove disposed about the inner periphery of said outer member, said inner member adapted to press-fit into said outer member groove when said members are brought into mating relationship with said prepuce held therebetween, whereby a crushing action is exerted upon said prepuce to cause hemostasis.

2. The dressing of claim 1 wherein said inner and outer members are made from one or more of a polymer, a rubber, or a metal.

3. The dressing of claim 2 wherein said inner and outer members are made from one or more of a polymer or a rubber.

4. The dressing of claim 1 wherein said inner and outer members are substantially planar in shape and each contains a bend outside of said plane to follow the frenulum of a penis.

5. The dressing of claim 1 wherein said outer member is scored adjacent one of its ends to permit it to be sized to accommodate different sized penises.

6. An adjustable circumcision dressing comprising:

(a) an inner arcuate member having a pair of ends, said inner member adapted to be positioned between the prepuce and shaft of a penis parallel to the corona of the glans of said penis and bearing a guard flange extending anteriorly beneath the prepuce to protect the penis from injury during circumscision;

(b) an elongate hollow connector piece adapted to receive said pair of ends of said inner member to accommodate different sized penises; and (c) an outer arcuate grooved member adapted to be positioned over and encompass the prepuce when it is pulled up over said inner member, said groove disposed about the inner periphery of said outer member, said inner member adapted to press-fit into said outer member groove when said members are brought into mating relationship with said prepuce held therebetween, whereby a crushing action is exerted upon said prepuce to cause hemostasis.

7. The dressing of claim 6 wherein said inner and outer members are made from one or more of a polymer, a rubber, or a metal.

8. The dressing of claim 7 wherein said inner and outer members are made from one or more of a polymer or a rubber.

9. The dressing of claim 6 wherein said inner and outer members are substantially planar in shape and each contains a bend outside of said plane to follow the frenulum of a penis.

10. The dressing of claim 6 wherein said outer member is scored adjacent one of its ends to permit it to be sized to accommodate different sized penises.

* * * * *